United States Patent
Chak et al.

(10) Patent No.: US 12,127,612 B2
(45) Date of Patent: Oct. 29, 2024

(54) ACCELERATOR FREE SYNTHETIC GLOVES WITH HIGH TEAR RESISTANCE

(71) Applicant: ANSELL LIMITED, Richmond (AU)

(72) Inventors: Choy Yuen Chak, Selangor (MY); Kai Yin Chong, Ipoh (MY); Wan Safarin Bin Wan Chik, Melaka (MY); Geraldo Alexandre Pimentel De Oliveira, Coimbra (PT)

(73) Assignee: Ansell Limited, Richmond (AU)

( * ) Notice: Subject to any disclaimer, the term of this patent is extended or adjusted under 35 U.S.C. 154(b) by 0 days.

(21) Appl. No.: 18/291,517

(22) PCT Filed: Jul. 27, 2022

(86) PCT No.: PCT/AU2022/050789
§ 371 (c)(1),
(2) Date: Jan. 23, 2024

(87) PCT Pub. No.: WO2023/004457
PCT Pub. Date: Feb. 2, 2023

(65) Prior Publication Data
US 2024/0260690 A1    Aug. 8, 2024

Related U.S. Application Data

(60) Provisional application No. 63/226,002, filed on Jul. 27, 2021.

(51) Int. Cl.
*A41D 19/00*    (2006.01)
*C08L 11/02*    (2006.01)

(52) U.S. Cl.
CPC .......... *A41D 19/0058* (2013.01); *C08L 11/02* (2013.01); *A41D 2500/54* (2013.01)

(58) Field of Classification Search
CPC .. A41D 19/055; A41D 19/0058; B32B 25/00; B32B 25/04; B32B 25/042; B32B 25/14;
(Continued)

(56) References Cited

U.S. PATENT DOCUMENTS

| | | | |
|---|---|---|---|
| 2006/0010565 A1 | 1/2006 | Teoh et al. | |
| 2015/0135403 A1 | 5/2015 | Mercado et al. | |

(Continued)

FOREIGN PATENT DOCUMENTS

| | | |
|---|---|---|
| CN | 105131380 A | 12/2015 |
| CN | 108884276 A | 11/2018 |

(Continued)

OTHER PUBLICATIONS

International Search Report and Written Opinion for PCT/AU2022/050789 dated Nov. 18, 2022.

*Primary Examiner* — Zachary M Davis
(74) *Attorney, Agent, or Firm* — Moser Taboada (57) ABSTRACT

Provided is a multilayer unsupported glove comprising: (A) an outer, first layer of polymer content comprising about 55 wt % or more chloroprene, from 0 wt % to up to about 45 wt % nitrile comprising carboxylated nitrile, and no more than about 5 wt % of another polymer; and (B) laminated to the outer layer, second layer of polymer content that is substantially nitrile 90 wt % or more, wherein the glove is about 0.16 mm or less in thickness, has a tensile strength unaged of greater than about 17 mPa pursuant to ASTM D412:2016 (E 2021) or a tensile strength aged of greater than about 23 MPa, and is accelerator free.

18 Claims, 2 Drawing Sheets

(58) Field of Classification Search
CPC ......... B32B 25/16; B32B 25/18; C08L 11/00;
C08L 11/02; C08L 13/00; C08L 13/02
See application file for complete search history.

(56) References Cited

U.S. PATENT DOCUMENTS

| | | |
|---|---|---|
| 2018/0016409 A1 | 1/2018 | Liou |
| 2019/0106554 A1 | 4/2019 | Muthusamy et al. |
| 2020/0087510 A1 | 3/2020 | Khoo |
| 2022/0016322 A1* | 1/2022 | Treilhes ................ A61L 31/041 |
| 2022/0135776 A1* | 5/2022 | Modha ............... A41D 19/0055 |
| | | 2/161.7 |

FOREIGN PATENT DOCUMENTS

| | | |
|---|---|---|
| CN | 111741690 A | 10/2020 |
| JP | 2012-040767 A | 3/2012 |
| WO | WO 99-24507 A1 | 5/1999 |
| WO | WO 2009-021229 A1 | 2/2009 |
| WO | WO2012085587 A1 | 6/2012 |
| WO | WO 2020-122704 A1 | 6/2020 |

* cited by examiner

ACCELERATOR FREE SYNTHETIC GLOVES WITH HIGH TEAR RESISTANCE

BACKGROUND

Field

The present application relates generally to unsupported gloves such as surgical and examination gloves.

Description of the Related Art

During surgery or examination procedures, gloves may be used for hours. Thus, comfort is a high priority as is integrity and resistance to sterilizing fluids. Polyisoprene gloves can provide substantial comfort, are free of allergy triggering proteins. However, for the most part they are not accelerator-free, nor are they as resistant to chemicals as nitrile or neoprene gloves. Nitrile and neoprene gloves, on the other hand, are generally not as comfortable as polyisoprene gloves.

Having the gloves be accelerator free adds to comfort by minimizing skin irritation. In addition, designing glove to include a useful elongation at break value assures that the glove is less likely to tear during the stresses inducing by operating surgical equipment. Further, the gloves need to be thin to provide greater dexterity, be resistant to tearing from the stress applied during sterile donning, be soft and comfortable, and have good grip. However, this mix of properties is not available with current nitrile or chloroprene-based gloves.

With the foregoing in view, the inventors herein provide multi-layer (e.g., two layer) laminate gloves that are accelerator free, have high tear resistance and good grip.

SUMMARY

Such laminate gloves, and methods for manufacturing the same, according to embodiments of the disclosure, substantially as shown in and/or described in connection with at least one of the figures, are disclosed. Various advantages, aspects, and novel features of the present disclosure will be more fully understood from the following description and drawings. The foregoing summary is not intended, and should not be contemplated, to describe each embodiment or every implementation of the present disclosure. Other and further embodiments of the present disclosure are described below. Furthermore, changes and modifications can be made to embodiments described herein without departing from the spirit and scope of the present disclosure and without diminishing the attendant advantages.

In one exemplary embodiment, is a two- to three-layer, unsupported glove comprising: (A) an outer, first layer of polymer content that consists of 55 wt % or more chloroprene, from 0 wt % to up to 45 wt % nitrile comprising carboxylated nitrile, and no more than about 5 wt % of another polymer; and (B) laminated to the outer layer, second layer of polymer content that is substantially nitrile 90 wt % or more, wherein the glove is 0.16 mm or less in thickness (or <0.15 mm, or <0.14 mm, or <0.13 mm), has a tensile strength unaged of greater than 17 mPa (or >18 MPa or >19 MPa) pursuant to ASTM D412:2016 (E 2021) or a tensile strength aged of greater than 23 MPa (or >24 MPa or >25 MPa), and is accelerator free, and wherein the glove is packaged (i) with the interior layer configured to the inside of the outer layer or (ii) folded to facilitate a user donning the glove with the interior layer to the inside of the outer layer.

DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only illustrative embodiments of this invention and are therefore not to be considered limiting of its scope, for the invention may admit to other equally effective embodiments.

To facilitate understanding, identical reference numerals have been used, where possible, to designate comparable elements that are common to the figures. The figures are not drawn to scale and may be simplified for clarity. It is contemplated that elements and features of one embodiment may be beneficially incorporated in other embodiments without further recitation.

DETAILED DESCRIPTION

At the outset, it should be noted that in the development of any such actual embodiment, numerous implementation-specific decisions must be made to achieve the developer's specific goals, such as compliance with system related and business related constraints, which will vary from one implementation to another. Moreover, it will be appreciated that such a development effort might be complex and time consuming but would nevertheless be a routine undertaking for those of ordinary skill in the art having the benefit of this disclosure. In addition, the composition used/disclosed herein can also comprise some components other than those cited. In the summary and this detailed description, each numerical value should be read once as modified by the term "about" (unless already expressly so modified), and then read again as not so modified unless otherwise indicated in context.

The following definitions are provided in order to aid those skilled in the art in understanding the detailed description.

As used in the specification and claims, "near" is inclusive of "at."

For use herein, the expressions "have", "may have", "include", "comprise", "may include", and "may comprise" indicate the existence of corresponding features (e.g., such as numeric values, functions, operations, or components) but do not exclude the presence of additional features.

For purposes herein, an article is "free" or "substantially free" from a material when no accelerator is intentionally added to the components from which the article is produced, and/or wherein a concentration of the material is less than about 0.01 wt % of the total weight of the article. For example, for purposes herein a glove is "accelerator free", also referred to herein as free from an accelerator, when no accelerator is intentionally added to the components from which the article is produced, and/or wherein a concentration of the accelerator is less than about 0.01 wt % of the article.

For purposes herein accelerator free refers to non-metallic crosslinking agents, such as sulfur based chemical accelerators including dithiocarbamates, thiurams, mercaptobenzothiazoles (MBT), and the like. Accordingly, a glove may be accelerator free if the rubber is crosslinked with a multi-valent metal ion e.g., Zn, Ti, Al, and/or the like.

For purposes herein, the term "nitrile" refers to an elastomer comprising polyacrylonitrile and butadiene moieties, i.e., polyacrylonitrile and butadiene rubber, also referred to herein as nitrile rubber.

For purposes herein, carboxylated nitrile, also referred to as carboxylated nitrile rubber, refers to a terpolymer of butadiene, acrylonitrile, and an unsaturated carboxylic acid or dicarboxylic acid, e.g., acrylic acid, methacrylic acid, crotonic acid, maleic acid, fumaric acid, or a combination thereof, and/or the like, wherein the resulting carboxylic acid groups allow for crosslinking of the polymer backbone through the addition of one or more metallic additives, sulfur, and/or the like.

For purposes herein, all percentages are by weight (i.e., wt %) based on the total weight of the particular part or layer of the article so limited, e.g., based on the total weight of a polymer layer referred to.

In the present disclosure, expressions such as, "A and/or B", "at least one of A and/or B", "one or more of A and/or B", and the like, refer to a case which may include any and all combinations of one or more of the associated listed items. For example, the terms "A and/or B", and "at least one of A or B" may refer to the case (1) where A is included, (2) where B is included, or (3) where both A and B are included.

Terms such as "first", "second", and the like used herein may refer to various elements of various embodiments disclosed herein, but it is to be understood that these labels do not limit the elements to any particular order, amount, or importance; such terms are used only to distinguish an element from another element and do not limit the order and/or priority of the elements. Likewise, such terms are used relative to others and do not represent absolute location, place, or order. For example, without departing from the scope of the present disclosure, a first element of one embodiment may be referred to as a second element in another embodiment, and similarly, a second element may be referred to as a first element.

Embodiments according to the instant disclosure are directed to multi-layer (e.g., at least two layer) laminate gloves having a chloroprene polymeric outside layer and a nitrile rubber layer laminated inside the chloroprene layer. In embodiments, these gloves, these gloves are cured using metal ion-mediated crosslinking, have the needed mix of properties which include being accelerator free, having high tear resistance, being soft and comfortable to the wearer for extended periods of time, and have good grip. In addition, if subjected to a mechanical simulation of the localized pull applied to the glove wrist when donning, the laminate gloves are much more resistant to tearing than are nitrile gloves of comparable thickness, and even more resistant relative to comparable chloroprene gloves. Accordingly, applicants have discovered a previously unknown symbiotic relationship between chloroprene and nitrile rubbers which when combined and arranged according to embodiments disclosed herein, the resulting glove has superior properties when compared to gloves formed from the individual components.

The predominantly polychloroprene (neoprene) first, outer layer of the gloves are crosslinked with metal oxide (e.g., divalent or trivalent), such as zinc oxide, lead oxide, trilead tetraoxide, and the like, as is known in the art. See, e.g., Smejda-Krzewicka et al., Polymer Bulletin volume 77, pages 4131-4146 (2020); US Pat. App. 2014/0011936. The latex suspension will generally include antioxidants, such as oligomerically hindered phenolic antioxidant.

The substantially nitrile (acrylonitrile butadiene) second, interior layer is typically also crosslinked with metal oxide (e.g., divalent or trivalent), such as zinc oxide, titanium oxide, aluminum oxide and the like. See, e.g., U.S. Pat. No. 7,005,478 B2, U.S. Pat. No. 10,954,364 B2, U.S. Pat. No. 10,023,718 B2.

The predominantly polychloroprene layers (i.e., comprising greater than 50 wt % polychloroprene) comprise in polymer content about 55 wt % or more chloroprene, from 0% to up to about 45 wt % nitrile comprising carboxylated nitrile, and no more than about 5 wt % of another polymer. Other polymers can be, for example natural rubber (NR), synthetic polyisoprene (PI), polyurethane (PU), butyl rubber (IIR or Butyl), styrene-butadiene rubber (SBR, e.g. carboxylated), Butyl and fluoroelastomer (FKM, also known as Viton®) combinations, or mixtures thereof. In embodiments, the layers are about 98 wt % or more, about 99 wt % or more, or 100 wt % polychloroprene in polymer content.

In embodiments, the nitrile comprises about 10 wt % or more of the predominantly polychloroprene layers, or about 20 wt % or more, or about 30 wt % or more (up to about 45 wt %). In embodiments, the nitrile comprises about 40 wt % or less of the predominantly polychloroprene layers, or about 30 wt % or less. (Unless otherwise specified, polymer compositions are relative to structural polymer content (not e.g. pigment or rheologic agents), and by weight.)

The predominantly polychloroprene layer can be, for example, about 75 micrometers (about 2.95 mil) to about 120 micrometers (about 4.7 mil) in thickness, measured at the middle of the palm.

The substantially nitrile layers are about 90 wt % or more nitrile. In embodiments, the substantially nitrile layers are about 95 wt % or more nitrile, or about 97 wt % or more, or about 98 wt % or more, or 100 wt %. Other polymers can be, for example chloroprene (CR), natural rubber (NR), synthetic polyisoprene (PI), polyurethane (PU), butyl rubber (IIR or Butyl), styrene-butadiene rubber (SBR, e.g. carboxylated), Butyl and fluoroelastomer combinations, or mixtures thereof. The degree of carboxylation can be an amount that promotes curing or chemical resistance to a second class of chemicals (e.g., weaker acids such as acetic acid, hydrocarbons, heptanes, hexanes, toluene, or xylenes). See U.S. Pat. No. 10,154,699 B2. One of skill will recognize that the amount of carboxylation can be tuned to the properties desired. For example, carboxylation can be at the lower end needed for curing or chemical resistance to help provide greater elasticity.

The polymers of the gloves can be selected to minimize allergens, such as found in gloves with NR or greater amounts of NR.

The substantially nitrile layer can be, for example, about 50 micrometers (about 2 mil) to about 80 micrometers (about 3.1 mil) in thickness, measured at the middle of the palm.

In embodiments, the gloves have a thin third layer interior to the substantially nitrile layer. For example, a polymer coating layer such as comprising polyurethane, polyacrylic, polyacrylonitrile, polyisoprene or blends or copolymers. The layer can be, for example, thinner than the first or second layers, or about 1 to about 20 micrometer in thickness (about 0.04 to about 0.8 mil), or about 5 to about 15 micrometer in thickness (about 0.2 to about 0.6 mil), or about 3 micrometer in thickness to about 5 micrometer in thickness (about 0.12 to about 0.2 mil).

The polymeric compositions optionally contain suitable additives, such as pH balancers, fillers, rheology modifiers, and the like to stabilize the polymeric compositions, or impart desired properties. The polymeric composition optionally contains commonly used stabilizers including but not limited to potassium hydroxide, ammonia, sulfonates, and others known to those of ordinary skill in the art. The polymeric composition may contain other commonly used ingredients such as surfactants, anti-microbial agents, fillers/additives for imparting various physical and chemical properties, and the like, known to those of ordinary skill in the art.

Figure 1A:
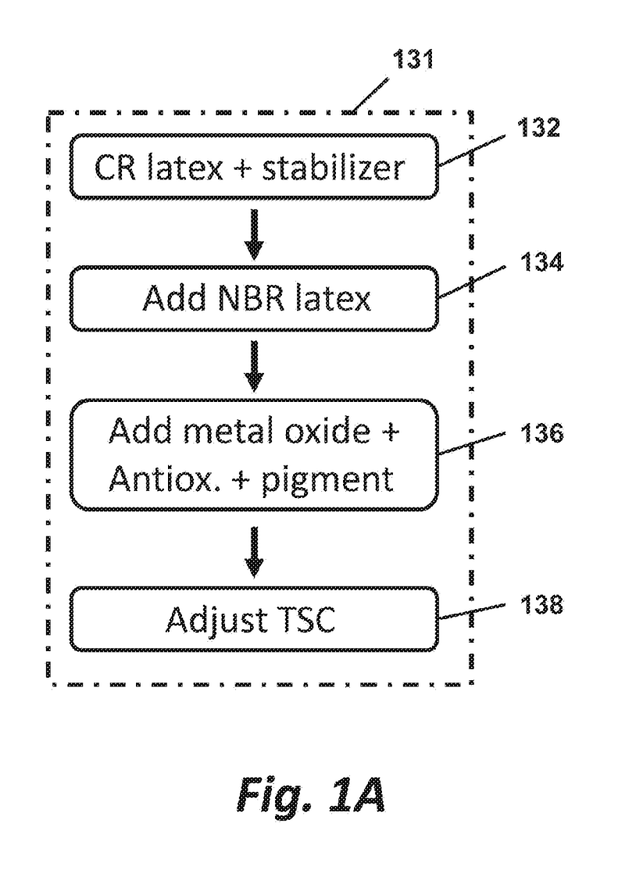
FIGS. 1A and 1B illustrate mixing of latices.
Figure 1B:
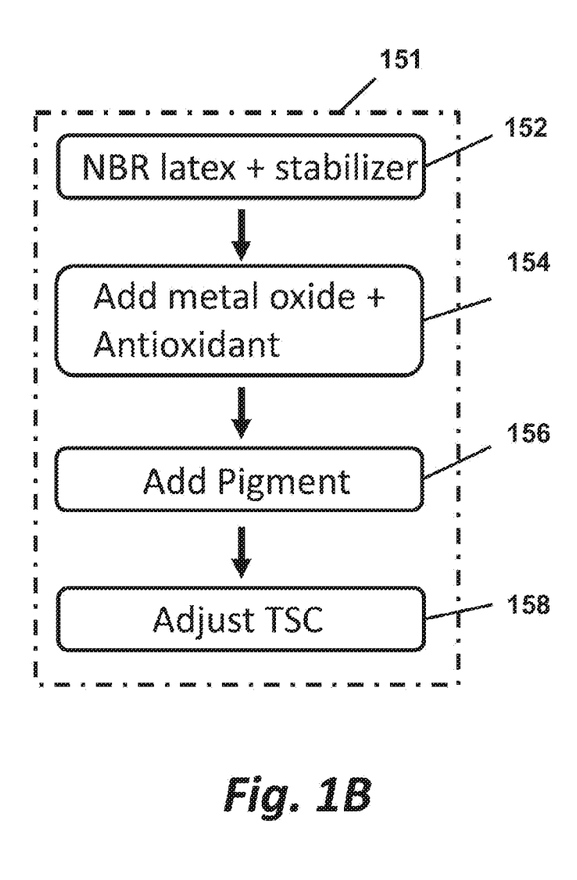

In conjunction with forming the gloves, the polymer dispersions are formulated, as exemplified in FIGS. 1A and 1B. In FIG. 1A, in process 131, the stabilized CR latex is provided, which can be as appropriately adjusted for TSC, in step 132. Then NBR latex is added in step 134. Other polymers may be added in conjunction with steps 132 or 134, or separately. In step 136, metal oxide, antioxidant and pigment are added. In step 138, the TSC to be used for dipping, such as about 18 to 35 wt %, is established, typically by adding water.

In FIG. 1B, in process 151, the stabilized NBR latex is provided, which can be as appropriately adjusted for TSC, in step 152. Then metal oxide and antioxidant are added in step 154. Other polymers may be added in conjunction with steps 152 or 154, or separately. In step 156, pigment is added. In step 158, the TSC to be used for dipping, such as about 18 to 35% by weight, is established, typically by adding water.

Figure 2:
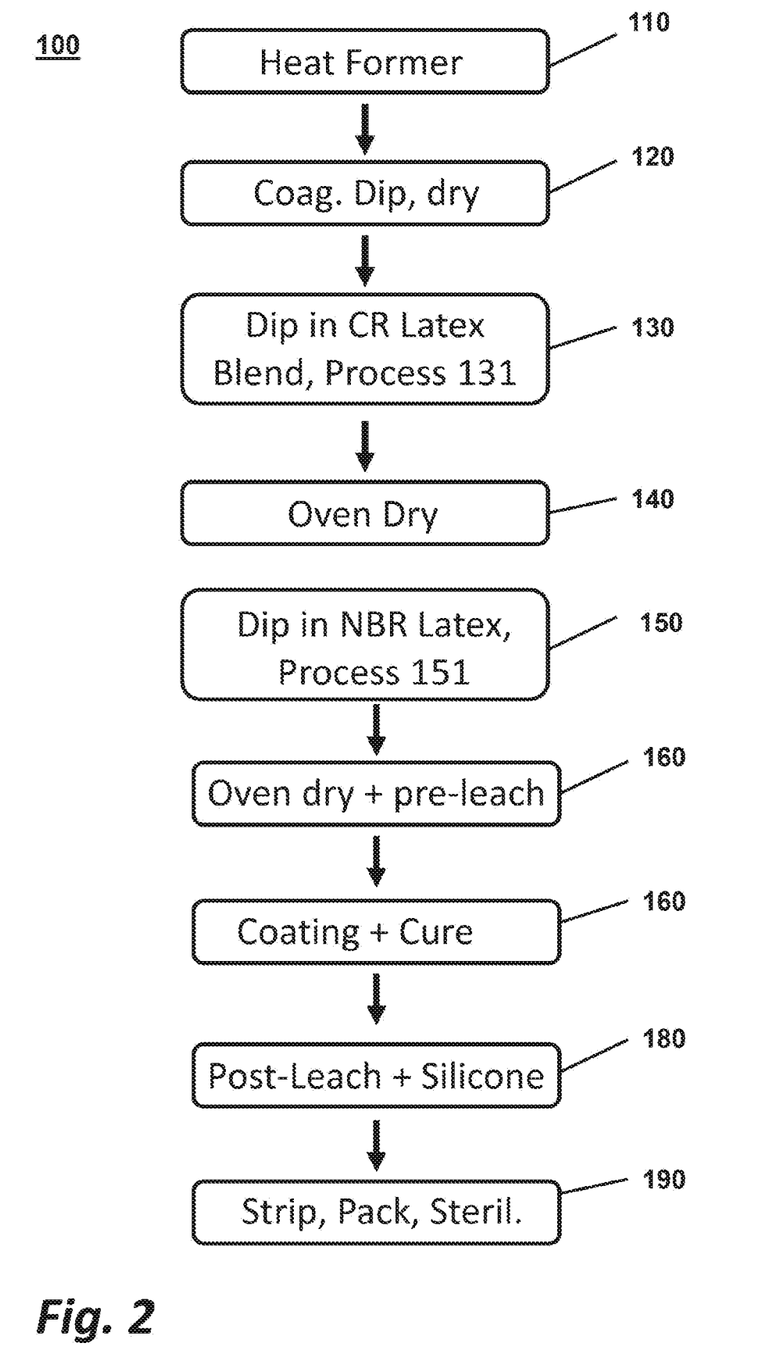
FIG. 2 illustrate the glove formation process.

The glove formation process, 100, is illustrated in FIG. 2. In step 110, the former is heated to dipping appropriate temperature. In step 120, the former is dipped in coagulant and oven dried. In step 130, the former is dipped in the polychloroprene latex, optionally a blend latex. In step 140, the former with CR coating is dried. In step 150, the former is dipped in the substantially NBR latex to form a second polymer coating. In step 160, the double-coated former is dried and pre-leached. In optional step 170, the coatings are further coated with another polymer layer (as described above) and cured. In step 180, the coatings are post-leached and siliconized. In step 190, the coatings, now a glove, are stripped from the former, the glove packaged and sterilized.

The gloves of the invention are unsupported. They can be examination or surgical gloves. As surgical gloves they can be presented in sterile packaging, generally one pair to the package (e.g., polypropylene lined packaging). Surgical gloves may be unique for the right and left glove to provide greater fit. As such, sleeves or separators in the packaging can be used to label the right and left, or the gloves may be labeled. Surgical gloves may be cuff folded to facilitate sterile donning procedures.

While tear strength is important, a repeated tugging process, a tear jig test, that mimics tugging on the glove cuff during donning can be a more important parameter. In embodiments, the aged or unaged gloves withstand substantially more such tugs without tearing than do nitrile gloves of comparable thickness and tear strength. In embodiments, the gloves resist 350 cycles or more in the tear jig test, or 400 cycles or more, or 425 cycles or more, or 450 cycles or more.

In embodiments, the glove grip (textured exterior side versus metal) is about 200 g/f (gram force) or more, or about 240 g/f or more, or about 260 g/f or more, or about 300 g/f or more. In embodiments, the glove grip is up to about 350 g/f. Texturing can be, for example, the raised diamond pattern texture type described in WO 2006/025843 A1; surfaces having with surfaces comprised of a plurality of convex protrusions or suction cup structures or a series of indentations made as described in U.S. Pat. No. 8,522,363 B2; or formed with the method of U.S. Pat. No. 10,500,797 B2.

For purposes herein the glove grip is determined using an in-house method with a IMADA friction meter under dry conditions, i.e., on a dry specimen.

For purposes herein, glove thickness is measured at the center of the palm, and in embodiments is about 0.16 mm or less, about 0.15 mm or less, or about 0.14 mm or less, or about 0.13 mm or less. The thickness can be about 0.11 mm or more, or about 0.12 mm or more.

In embodiments, the gloves have an unaged tensile strength of about 17 MPa or higher (ASTM D412:2016 (E 2021)), or about 18 MPa or higher, or about 19 MPa or higher. In embodiments, the gloves have an unaged tensile strength of about 9 N or higher (EN 455-2:2015), or about 9.5 N or higher, or about 10 N or higher.

In embodiments, the gloves have an aged tensile strength of 23 MPa or higher (ASTM D412:2016 (E 2021)), or 24 MPa or higher, or 26 MPa or higher (accelerated aging at 70° C. for 7 days). In embodiments, the gloves have an aged tensile strength of 9 N or higher (EN 455-2:2015), or 10 N or higher, or 11 N or higher.

In embodiments, the gloves have an isopropyl alcohol (IPA) resistance (EN 16523-1:2015) of Level 2 or higher. This represents a breakthrough time of 30 minutes or longer. Samples are preconditioned for at least 16 h at a temperature of 23+/−2 deg C. The assembled permeation cell is placed in a temperature controlled room at similar temperature.

In embodiments, the elongation at break of the aged and unaged gloves is about 650% based on the initial length of the sample or higher, or about 700% or higher (ASTM D412:2016)

In embodiments, the tensile stress modulus at 500% of the aged or unaged gloves is about 7 MPa or lower, or about 6 MPa or lower, or about 5 MPa or lower, or about 4.7 MPa or lower (ASTM D412:2016).

In embodiments, the puncture resistance of the unaged gloves is about 65 N/mm or more, or about 70 N/mm or more, or about 75 N/mm or more when determined according to SNZ AS/NZS 4179:2014.

In embodiments, the stress retention (i.e., stress relaxation) of the unaged gloves is about 42% or higher, or about 45% or higher, or about 48% or higher, when determined according to ASTM D412:2016 (E 2021).

In embodiments, the tear strength of the unaged gloves is about 16 N/mm or higher, or about 18 N/mm, or about 20 N/mm (when determined according to ASTM D624 TYPE C:2000 (R2020)).

Embodiments

The following embodiments are contemplated herein.

E1. An unsupported glove comprising:
an outer, first layer of polymer content comprising 55 wt % or more chloroprene, from 0 wt % to about 45 wt % nitrile rubber; and less than or equal to about 5 wt % of another polymer, if another polymer is present; and
laminated to the outer layer, a second layer of polymer content comprising greater than or equal to about 90 wt % nitrile rubber,
the glove having a thickness of less than or equal to about 0.16 mm when determined at a middle of a palm portion of the glove,
a tensile strength unaged of greater than or equal to about 17 mPa when determined according to ASTM D412: 2016 (E 2021);
E2. The unsupported glove according to embodiment E1, having a tensile strength of greater than or equal to about 23

MPa when determined according to ASTM D412:2016 (E 2021) after aging at about 70° C. for 7 days.

E3. The unsupported glove according to embodiment E1 or E2, wherein the nitrile rubber comprises a carboxylated nitrile rubber.

E4. An unsupported glove comprising:
an outer, first layer of polymer content comprising 55 wt % or more chloroprene, from 0 wt % to up to 45 wt % nitrile comprising carboxylated nitrile, and no more than about 5 wt % of another polymer; and laminated to the outer layer, second layer of polymer content that is substantially nitrile 90 wt % or more,
wherein the glove is about 0.16 mm or less in thickness, has a tensile strength unaged of greater than about 17 mPa pursuant to ASTM D412:2016 (E 2021) or a tensile strength aged of greater than about 23 MPa when aged at about 70° C. for 7 days, and is accelerator free.

E5. The unsupported glove according to any one of embodiments E1 through E4, wherein the outer, first layer of polymer content consists of greater than or equal to about 55 wt % chloroprene, from 0 wt % to greater than or equal to about 45 wt % nitrile rubber comprising carboxylated nitrile rubber, and less than or equal to about 5 wt % of another polymer, if any.

E6. The unsupported glove according to any one of embodiments E1 through E5, wherein a glove durability is greater than or equal to about 350 cycles when determined according to a tear jig test.

E7. The unsupported glove according to any one of embodiments E1 through E6, wherein the first layer of polymer comprises greater than or equal to about 20 wt % nitrile rubber.

E8. The unsupported glove according to any one of embodiments E1 through E7, wherein the first layer polymer content comprises about 30 wt % or more nitrile.

E9. The unsupported glove according to any one of embodiments E1 through E8, wherein the first layer thickness is about 0.075 mm to about 0.12 mm.

E10. The unsupported glove according to any one of embodiments E1 through E9, wherein the second layer thickness is about 0.05 mm to about 0.08 mm.

E11. The unsupported glove according to any one of embodiments E1 through E10, comprising a third layer thinner than the first and second.

E12. The unsupported glove according to any one of embodiments E1 through E 11, wherein the glove thickness is from about 0.12 mm to about 0.14 mm.

E13. The unsupported glove according to any one of embodiments E1 through E12, wherein the glove grip is about 200 g/f or more.

E14. The unsupported glove according to any one of embodiments E1 through E13, wherein the second layer polymer content comprises about 90 wt % or more nitrile.

E15. The unsupported glove according to any one of embodiments E1 through E14, wherein the IPA resistance is level 2 or higher.

E16. The unsupported glove according to any one of embodiments E1 through E15, wherein the unaged tear strength is about 16 N/mm or more, when determined according to ASTM D624 TYPE C:2000 (R2020)).

E17. The unsupported glove according to any one of embodiments E1 through E16, wherein unaged the puncture resistance is about 65 N/mm or more, when determined according to SNZ AS/NZS 4179:2014.

E18. The unsupported glove according to any one of embodiments E1 through E17, wherein aged or unaged the elongation at break is about 650% or more.

E19. The unsupported glove according to any one of embodiments E1 through E18, wherein the aged or unaged tensile strength modulus at 500% is about 7 MPa or less.

E20. The unsupported glove according to any one of embodiments E1 through E19, wherein the unaged stress retention is about 42% or more, when determined according to ASTM D412:2016 (E 2021).

E21. The unsupported glove according to any one of embodiments E1 through E20, wherein the unsupported glove is packaged (i) with the interior layer configured to the inside of the outer layer or (ii) folded to facilitate a user donning the unsupported glove with the interior layer to the inside of the outer layer.

E22. An unsupported glove according to any one of embodiments E1 through E21, having two or more layers.

E23. An unsupported glove according to any one of embodiments E1 through E21, having three or more layers.

E24. An unsupported glove according to any one or combination of embodiments disclosed herein.

Specific embodiments according to the methods of the present invention will now be described in the following examples. The examples are illustrative only, and are not intended to limit the remainder of the disclosure in any way.

All ranges recited herein include ranges therebetween and can be inclusive or exclusive of the endpoints. Optional included ranges are from integer values therebetween (or inclusive of one original endpoint), at the order of magnitude recited or the next smaller order of magnitude. For example, if the lower range value is 0.2, optional included endpoints can be 0.3, 0.4, . . . 1.1, 1.2, and the like, as well as 1, 2, 3 and the like; if the higher range is 8, optional included endpoints can be 7, 6, and the like, as well as 7.9, 7.8, and the like. One-sided boundaries, such as 3 or more, similarly include consistent boundaries (or ranges) starting at integer values at the recited order of magnitude or one lower. For example, 3 or more includes 4 or more, or 3.1 or more. If there are two ranges mentioned, such as about 1 to 10 and about 2 to 5, those of skill will recognize that the implied ranges of 1 to 5 and 2 to 10 are within the invention.

A laminate is a bonding, fusing, adhesion, or the like between polymer layers, or between polymer and fabric layers, such that in the range of anticipated use the laminate is a unitary structure.

Where a sentence states that its subject is found in embodiments, or in certain embodiments, or in the like, it is applicable to any embodiment in which the subject matter can be logically applied.

Glove grip was measured with a IMADA friction meter (IMADA Horizontal Motorized Test Stand MH2-500N, IMADA Mountable Digital Force Gauge ZT Series and IMADA Force Recorder Standard (COF Ver.) Software Version 1.01).

The principle of the test method relies on frictional resistance to the relative motion of two solid objects being proportional to the force that presses the surfaces together as well as the roughness of the surfaces. The force perpendicular or "normal" to the surfaces that affects the frictional resistances and typically called the "normal force" and designated by N. The frictional resistance force is then determined according to formula (II):

$$f_{friction} = m * N, \text{ wherein } m = \text{coefficient of friction} \quad (II).$$

The frictional force is also presumed to be proportional to the coefficient of friction. However, the amount of force required to move an object starting from rest is usually greater than the force required to keep it moving at constant velocity once it is started. Rougher surfaces will experience more friction as compared to smoother surfaces. Thus, higher friction values mean better grip property of those tested specimen.

Sample Preparation and Test Method.

The test specimen used for testing was cut out from a representative portion of the back palm area of the glove sample and made sure to be free of holes, blisters, creases and other imperfections.

One test piece is cut from each glove and minimum 7 pieces of each lot sample size were required.

All tests were carried out at 20-25° C. and 45-55% relative humidity in which the test specimen is conditioned for at least 24 hours before testing.

A rectangular test specimen was clamped on a metal plane and other glove with rhombus shape wraps a flat metal dead weight then placed on a rectangular test specimen. The determined wrap flat metal dead weight was then pulled by IMADA force gauge until it reaches to 15 mm mark.

Measurement of friction values was read by IMADA Horizontal Motorized Test Stand MH2-500N. The data were displayed in graphs and analyzed by the transferring system up to maximum 2000 data points per second.

The stress retention test was determined according to ASTM D412:2016 (E 2021), which is referred to as the stress retention or stress relaxation, wherein a decrease in stress in a material subjected to prolonged constant strain. The principle of the test method is that when a constant strain is applied to a rubber sample, the force necessary to maintain that strain is not constant but decreases with time. This behavior is called "stress retention" or "stress relaxation".

The processes causing stress retention may be physical (e.g. thermal degradation) or chemical in nature, and under all normal conditions both types of process will occur simultaneously. However, at normal or low temperatures and/or short times, stress retention is dominated by physical processes; while at high temperatures and/or long times, chemical processes are dominant.

The test method includes the following steps:

Specimens are cut in the shape of dumbbells test pieces using ASTM D412 Die C.

The median of thickness is determine and measure from the three position of the dumbbell specimen—use to calculate the cross sectional area.

Dumbbell samples prepared are clamped and stressed to 100% of their initial length with a Shimadzu Universal Testing Machine. The amount of stress required to maintain this stretch is then recorded every minute for 30 minutes.

The resulting data are then plotted on graph with "Average stress versus time" and "Average percent of initial stress versus time".

Two dumbbells are tested from the same sample for each log/batch. If the difference between the two dumbbells is more than 10%, test another dumbbell from the same sample. The average result is taken from the three specimens.

Calculation:

The % of initial stress for specimen is equal to the following formula (i):

$$\frac{\text{Stress}}{\text{Initial stress(at 0 minute)}} \times 100 \qquad (I)$$

Glove durability was measured by a "tear jig test" using a Pull Jig Tester, an instrument known in the art to measure the resistance of tear during donning the gloves. The pull jig tester is configured to simulate donning activities by counting the numbers of pulls for the glove to tear. It uses a piston (an automatic servo-driven system) in the tester to pull a clamped portion of the glove worn on a former. The glove is clamped or gripped at the cuff area. When the piston pulls (away horizontally from the cuff), it stretches the gloves simulating a donning action. The piston retracts back to the original position and then pulls another cycle. The distance pulled is 150 mm. This cycle repeats until the glove tear and the number of pulls are recorded.

This invention described herein is of a glove and methods of forming the same. Although some embodiments have been discussed above, other implementations and applications are also within the scope of the following claims. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims. More specifically, those of skill will recognize that any embodiment described herein that those of skill would recognize could advantageously have a sub-feature of another embodiment, is described as having that sub-feature Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

The invention claimed is:

1. An unsupported glove comprising:
an outer, first layer of polymer content comprising greater than or equal to about 55 wt % chloroprene, from 0 wt % to less than or equal to 45 wt % nitrile rubber comprising carboxylated nitrile rubber, and less than or equal to about 5 wt % of another polymer; and
laminated to the outer layer, a second layer of polymer content comprising greater than or equal to about 90 wt % nitrile rubber,
wherein the glove has a thickness of less than or equal to about 0.16 mm, an unaged tensile strength of greater than or equal to about 17 mPa when determined according to ASTM D412:2016 (E 2021) and/or an aged tensile strength of greater than or equal to about 23 Mpa, and is free from an accelerator.

2. The unsupported glove of claim 1, wherein the unsupported glove is packaged (i) with an interior layer configured to the inside of an outer layer or (ii) folded to facilitate a user donning the unsupported glove with the interior layer to the inside of the outer layer.

3. The unsupported glove of claim 1, wherein the outer, first layer of b polymer content consists of greater than or equal to about 55 wt % chloroprene, from 0 wt % to less than or equal to 45 wt % nitrile rubber comprising carboxylated nitrile rubber, and less than or equal to about 5 wt % of another polymer, if any.

4. The unsupported glove of claim 1, wherein a glove durability is greater than or equal to about 350 cycles when determined according to a tear jig test.

5. The unsupported glove of claim 1, wherein the first layer of polymer content comprises greater than or equal to about 20 wt % nitrile rubber.

6. The unsupported glove of claim 1, wherein the first layer of polymer content comprises about 30 wt % or more nitrile rubber.

7. The unsupported glove of claim 1, wherein the first layer thickness is about 0.075 mm to about 0.12 mm.

8. The unsupported glove of claim 1, wherein the second layer thickness is about 0.05 mm to about 0.08 mm.

9. The unsupported glove of claim 1, comprising a third layer thinner than the first and second layers.

10. The unsupported glove of claim 1, wherein the glove thickness is from about 0.12 mm to about 0.14 mm.

11. The unsupported glove of claim 1, wherein the glove grip is about 200 g/f or more.

12. The unsupported glove of claim 1, wherein the second layer of polymer content comprises about 90 wt % or more nitrile rubber.

13. The unsupported glove of claim 1, wherein the isopropyl alcohol resistance is level 2 or higher.

14. The unsupported glove of claim 1, wherein the unaged tear strength is about 16 N/mm or more, when determined according to ASTM D624 TYPE C:2000 (R2020)).

15. The unsupported glove of claim 1, wherein unaged the puncture resistance is about 65 N/mm or more, when determined according to SNZ AS/NZS 4179:2014.

16. The unsupported glove of claim 1, wherein aged or unaged the elongation at break is about 650% or more.

17. The unsupported glove of claim 1, wherein the aged or unaged tensile strength modulus at 500% is about 7 MPa or less.

18. The unsupported glove of claim 1, wherein the unaged stress retention is about 42% or more.

* * * * *

UNITED STATES PATENT AND TRADEMARK OFFICE
CERTIFICATE OF CORRECTION

| | | |
|---|---|---|
| PATENT NO. | : 12,127,612 B2 | Page 1 of 1 |
| APPLICATION NO. | : 18/291517 | |
| DATED | : October 29, 2024 | |
| INVENTOR(S) | : Choy Yuen Chak et al. | |

It is certified that error appears in the above-identified patent and that said Letters Patent is hereby corrected as shown below:

In the Claims

In Claim 3, Column 10, Line 63, please delete "b"

Signed and Sealed this
Thirty-first Day of December, 2024

Derrick Brent
*Acting Director of the United States Patent and Trademark Office*